US006932601B2

(12) United States Patent
Frider et al.

(10) Patent No.: US 6,932,601 B2
(45) Date of Patent: Aug. 23, 2005

(54) DENTAL EVACUATION MIRROR

(76) Inventors: Debra Kay Frider, 3602 Westmoor Dr., Moorhead, MN (US) 56560; Paula Ann Wilson, 2169 Victoria Rose Dr., Fargo, ND (US) 58104

( * ) Notice: Subject to any disclaimer, the term of this patent is extended or adjusted under 35 U.S.C. 154(b) by 0 days.

(21) Appl. No.: 10/716,383

(22) Filed: Nov. 18, 2003

(65) Prior Publication Data

US 2005/0106527 A1    May 19, 2005

(51) Int. Cl.⁷ .................................................. A61C 3/00
(52) U.S. Cl. .......................................... 433/31; 433/93
(58) Field of Search ............................. 433/30, 31, 91, 433/93

(56) References Cited

U.S. PATENT DOCUMENTS

| | | | |
|---|---|---|---|
| 2,436,040 A | * | 2/1948 | Friedman ..................... 433/30 |
| 3,052,031 A | | 9/1962 | Piscitelli |
| 3,092,910 A | * | 6/1963 | Warriner ..................... 433/31 |
| 3,102,338 A | | 9/1963 | Warriner |
| 3,631,598 A | * | 1/1972 | Lussier ....................... 433/31 |
| 3,928,916 A | | 12/1975 | Hansson |
| 3,969,824 A | | 7/1976 | Widen et al. |
| 3,986,266 A | | 10/1976 | Vellender |
| 4,511,329 A | | 4/1985 | Diamond |
| 4,521,185 A | | 6/1985 | Cohen |
| 4,925,391 A | * | 5/1990 | Berlin ........................ 433/31 |
| D320,075 S | * | 9/1991 | Berlin ...................... D24/112 |
| 5,281,134 A | | 1/1994 | Schultz |
| 5,295,826 A | | 3/1994 | Yandell et al. |
| 5,449,290 A | | 9/1995 | Reitz |
| 5,813,856 A | | 9/1998 | Lee |
| 5,951,284 A | * | 9/1999 | Lake ........................... 433/31 |
| 6,247,924 B1 | | 6/2001 | Gunnarsson |

FOREIGN PATENT DOCUMENTS

| | | |
|---|---|---|
| DE | 198 46 298 | 4/2000 |
| DE | 103 40 278 A1 * | 4/2004 |
| EP | 0 314 657 A1 * | 5/1989 |
| FR | 2 595 939 | 9/1987 |
| FR | 2 620 930 A1 * | 3/1989 |
| FR | 2 642 298 | 8/1990 |
| JP | 7-136110 | 5/1995 |
| JP | 7-289570 | 11/1995 |
| JP | 10-192309 | 7/1998 |
| SE | 470 486 | 5/1994 |
| WO | WO 00/12025 | 3/2000 |

* cited by examiner

Primary Examiner—Ralph A. Lewis
(74) Attorney, Agent, or Firm—Dorsey & Whitney LLP (57) ABSTRACT

The present invention is a dental evacuation tool for being placed in fluid communication with a dental vacuum. The tool comprises a suction head and an elongated tubular handle. The suction head includes a mirror surface, first and second upward-facing intake orifices adjacent the mirror surface, and an exit fluid pathway that is in fluid communication with the first and second upward-facing intake orifices. The elongated tubular handle includes a first end adapted to be in fluid communication with the vacuum and a second end in fluid communication with the exit fluid pathway. The first and second upward-facing intake orifices are positioned generally opposite each other about the mirror surface, are generally centered about a line that is generally perpendicular to the longitudinal axis of the handle, and open in generally the same direction faced by the mirror.

10 Claims, 5 Drawing Sheets

FIG.9b

DENTAL EVACUATION MIRROR

TECHNICAL FIELD

The present invention relates to dental instruments and methods of making and using dental instruments. More specifically, the present invention relates to dental evacuation mirrors and methods of making and using dental evacuation mirrors.

BACKGROUND OF THE INVENTION

A dental professional will typically sit while performing a dental procedure. To avoid neck strain, the dental professional will utilize a dental mirror to indirectly view the interior of a patient's mouth.

Dental procedures result in the accumulation of liquids and debris within the patient's mouth. A dental professional uses a dental evacuator to vacuum the liquids and debris from the patient's mouth.

Most dental procedures require both a dental mirror and a dental evacuator. Consequently, the features of a dental mirror and a dental evacuator were combined to form prior art dental evacuator mirrors. Unfortunately, the configurations of those prior art devices often cause them to suck in the soft, pliable tissue of a patient's mouth. This is uncomfortable for a patient and impedes the evacuation of fluids and debris. Also, the configurations of the prior art dental evacuator mirrors are such that they require a dental professional to contort their arms excessively to evacuate fluids and debris from a patient's mouth.

There is a need in the art for a dental evacuation mirror that is more comfortable for the patient. Also, there is a need in the art for a dental evacuation mirror that is easier and more comfortable to use for a dental professional.

BRIEF SUMMARY OF THE INVENTION

The present invention, in one embodiment, is a dental evacuation tool for being placed in fluid communication with a dental vacuum. The tool comprises a suction head and an elongated tubular handle. The suction head includes a mirror surface, first and second upward-facing intake orifices adjacent the mirror surface, and an exit fluid pathway that is in fluid communication with the first and second upward-facing intake orifices. The elongated tubular handle includes a first end adapted to be in fluid communication with the vacuum and a second end in fluid communication with the exit fluid pathway. The first and second upward-facing intake orifices are positioned generally opposite each other about the mirror surface, are generally centered about a line that is generally perpendicular to the longitudinal axis of the handle, and open in generally the same direction faced by the mirror.

The present invention, in another embodiment, is a dental evacuation tool for being placed in fluid communication with a dental vacuum. The tool comprises a suction head and an elongated tubular handle. The suction head includes a mirror surface, a first intake orifice adjacent the edge of the mirror surface and having a center point, a second intake orifice adjacent the edge of the mirror surface and having a center point, and an exit fluid pathway that is in fluid communication with the first and second intake orifices. The elongated tubular handle includes a first end adapted to be in fluid communication with the vacuum and a second end in fluid communication with the exit fluid pathway. The center point of the first intake orifice is radially offset by approximately 45 to approximately 135 degrees in a first direction about the edge of the mirror surface from the center of the exit fluid pathway. The center point of the second intake orifice is radially offset by approximately 45 to approximately 135 degrees in a second direction about the edge of the mirror surface from the center of the exit fluid pathway. The first and second intake orifices radially extend by approximately one to approximately 90 degrees away from each side of their respective center points. The first and second intake orifices open in a direction that is approximately zero to approximately 45 degrees from being normal to the mirror surface.

The present invention, in another embodiment, is a method of making a dental evacuation tool for being placed in fluid communication with a dental vacuum. The method comprises providing a suction head, an elongated tubular handle, and first and second upward-facing intake orifices. The suction head is to include a mirror surface and an exit fluid pathway. The elongated tubular handle is to include a first end in fluid communication with the exit fluid pathway and a second end adapted to be in fluid communication with the vacuum. The first and second upward-facing intake orifices are to be on the suction head adjacent to the mirror surface such that the upward-facing intake orifices are in fluid communication with the exit fluid pathway. Furthermore, the first and second upward-facing intake orifices are to be positioned generally opposite each other about the mirror surface, are to be generally centered about a line that is generally perpendicular to the longitudinal axis of the handle, and are to open in generally the same direction faced by the mirror.

The present invention, in another embodiment, is a method of using a dental evacuation mirror that has a suction head. The suction head has a mirror surface, a backside opposite the mirror surface, and an intake orifice adjacent to the mirror surface. The method comprises placing the suction head in a first position within the mouth of a person and, while maintaining the suction head in the first position, evacuating fluids and/or debris through the intake orifice without suctioning a cheek. The first position is between the cheek and a buccal surface of a tooth, wherein the mirror surface is adjacent to the buccal surface and the backside abuts against and retracts the cheek.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
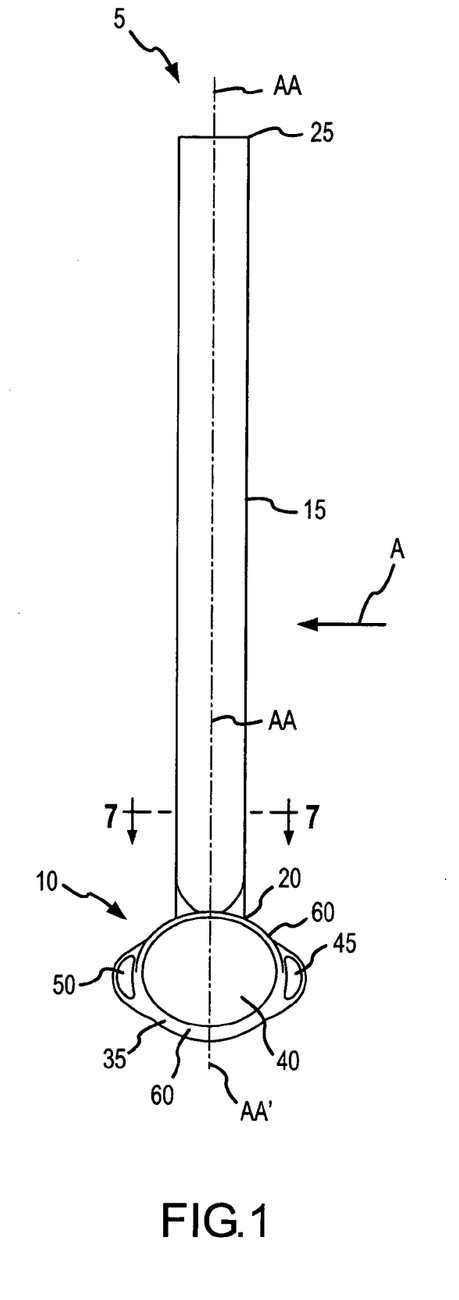
FIG. 1 is a top view of the dental evacuation mirror, wherein the viewing direction is perpendicular to the longitudinal axis of the elongated tubular handle.
Figure 2:
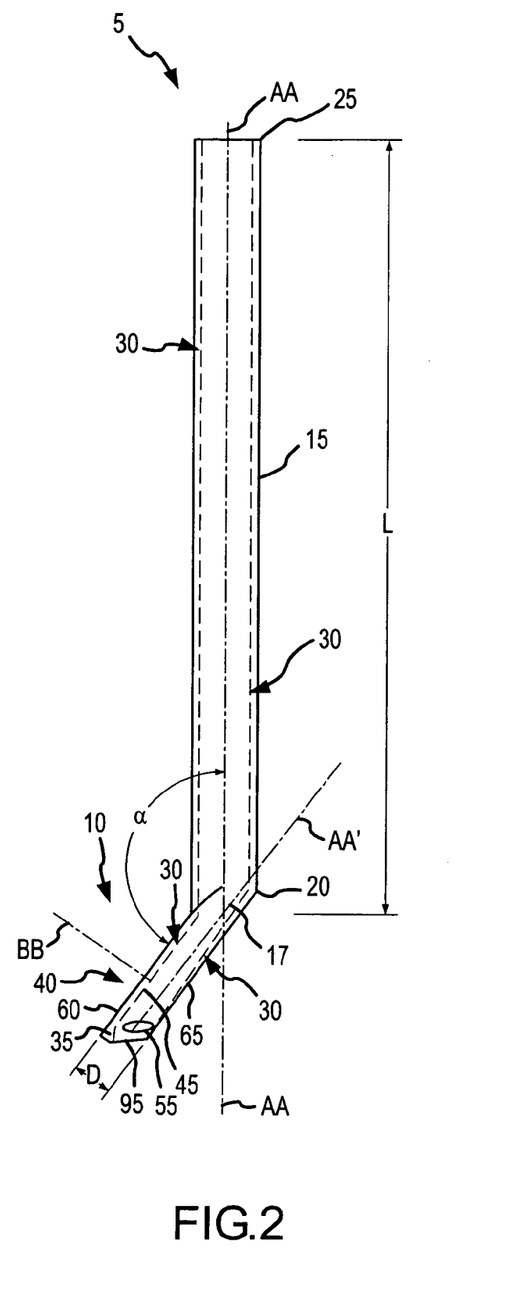
FIG. 2 is a side elevation of the dental evacuation mirror as viewed from the direction of arrow A in FIG. 1.

FIG. 1 is a top view of a dental evacuation mirror 5 including a suction head 10 and an elongated tubular handle 15. In FIG. 1, the dental evacuation mirror 5 is viewed from a direction that is perpendicular to the longitudinal axis AA of the handle 15. FIG. 2 is a side elevation of the dental evacuation mirror 5 as viewed from the direction of arrow A in FIG. 1.

Figure 7:
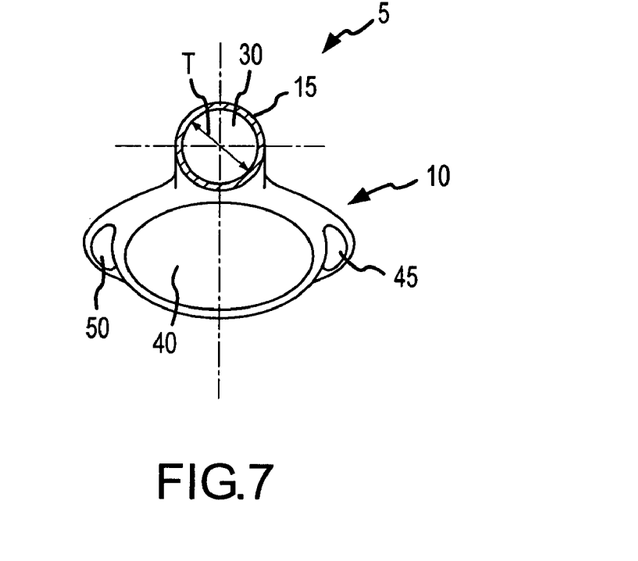
FIG. 7 is a sectional view taken through the elongated tubular handle as shown in FIG. 1.

As shown in FIGS. 1 and 2, the handle 15 has a first end 20 connected to an exit fluid pathway 17 of the suction head 10 and a second end 25 that is adapted to be placed in fluid communication with a dental vacuum. As illustrated in FIG. 2 by phantom lines, the suction head 10 and the handle 15 are hollow in that a void or channel 30 extends from the second end 25, through the length of the handle 15, and into the suction head 10. As indicated in FIG. 7, which is a sectional view taken through the elongated tubular handle 15 as shown in FIG. 1, the void or channel 30 has a diameter T of between approximately 0.25 inches and approximately 0.65 inches. In one embodiment, the diameter T is between approximately 0.35 inches and approximately 0.55 inches. In one embodiment, the diameter T is between approximately 0.40 inches and approximately 0.45 inches. In one embodiment, the diameter T is approximately 0.44 inches.

As shown in FIGS. 1 and 2, the suction head 10 includes a housing 35, a mirror surface 40, a first upward-facing intake orifice 45, a second upward-facing intake orifice 50, and forward-facing intake orifices 55. The housing 35 supports the mirror surface 40 and the orifices 45, 50, 55 are formed in the housing 35. The intake orifices 45, 50, 55 open into the void or channel 30 within the housing 35. Thus, when the dental evacuation mirror 5 is connected to a dental vacuum, the orifices 45, 50, 55 are placed in fluid communication with the dental vacuum via the void or channel 30. The void or channel 30 forms a continuous fluid communication pathway that leads from the orifices 45, 50, 55, through the suction head 10 and the handle 15, and into the dental vacuum.

The suction head 10 and the handle 15 of the dental evacuation mirror 5 may be made of various materials, such as metal, polymer, ceramic, glass, etc., or combinations thereof. Depending on the material, the dental evacuation mirror 5 may be machined, molded, or extruded. The mirror surface 40 may be a metal reflective surface or a non-metal reflective surface such as a glass mirror.

As indicated in FIG. 2, the longitudinal axis AA of the elongated tubular handle 15 forms an angle $\alpha$ with the plane formed by the mirror surface 40. As can be seen in FIGS. 1 and 2, the longitudinal axis AA' of the suction head 10 is parallel to the mirror surface 40 and coplanar with the longitudinal axis AA of the handle 15. Thus, the longitudinal axis AA of the handle 15 will also form angle $\alpha$ with the longitudinal axis AA' of the suction head 10.

In one embodiment the angle $\alpha$ is between approximately 130° and approximately 160°. In one embodiment, the angle $\alpha$ is between approximately 135° and approximately 155°. In one embodiment, the angle $\alpha$ is between approximately 140° and approximately 150°. In one embodiment, the angle $\alpha$ is approximately 145°.

As illustrated in FIG. 2, in one embodiment, the handle 15 has a length L of between approximately 7.5 inches and approximately 4.0 inches. In another embodiment, the handle 15 has a length L of between approximately 7.0 inches and approximately 4.5 inches. In another embodiment, the handle 15 has a length L of between approximately 6.5 inches and approximately 5.0 inches. In another embodiment, the handle 15 has a length L of between approximately 6.0 inches and approximately 5.5 inches.

As shown in FIG. 2, in one embodiment, the top edge 60 of the housing 35 (i.e., the edge of the housing 35 boarding the edge of the mirror surface 40) and the backside 65 of the housing 35 are offset by a distance D of between approximately 0.15 inches and approximately 0.40 inches. In another embodiment, the top edge 60 and the backside 65 are offset by a distance D of between approximately 0.20 inches and approximately 0.35 inches. In another embodiment, the top edge 60 and the backside 65 are offset by a distance D of between approximately 0.25 inches and approximately 0.30 inches. In another embodiment, the top edge 60 and the backside 65 are offset by a distance D of approximately 0.28 inches.

Figures 3, 4, 5:
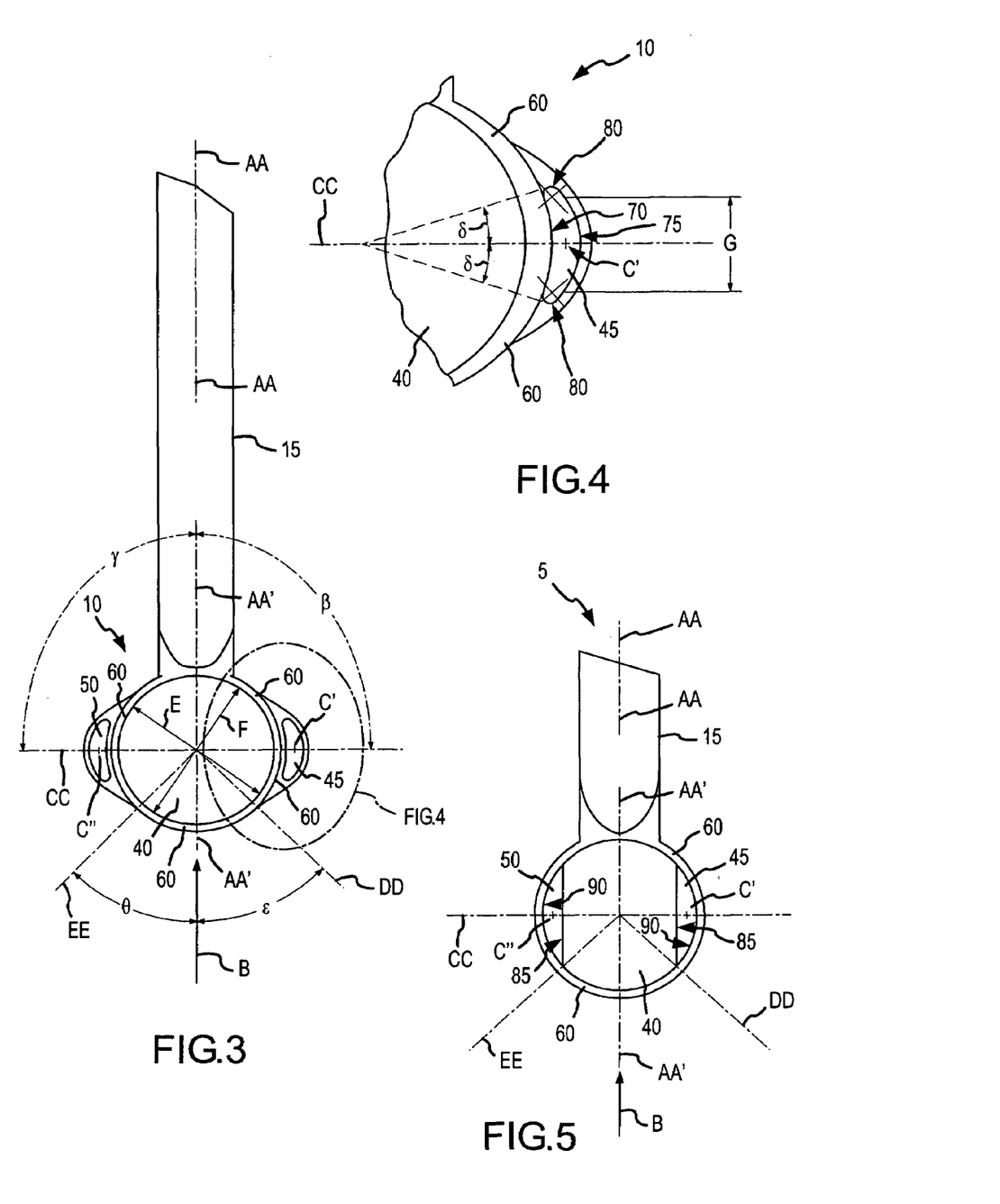
FIG. 3 is a top view of the dental evacuation mirror, wherein the viewing direction is perpendicular to the mirror surface.
FIG. 4 is an enlarged view of the right intake orifice depicted in FIG. 3.
FIG. 5 is a top view of another embodiment of the dental evacuation mirror, wherein the viewing direction is perpendicular to the mirror surface.

To further describe the features of the suction head 10, reference is now made to FIGS. 3 and 4. FIG. 3 is a top view of the dental evacuation mirror 5, wherein the viewing direction is perpendicular to the mirror surface 40. FIG. 4 is an enlarged view of the first upward-facing intake orifice 45 depicted in FIG. 3.

As shown in FIG. 3, in one embodiment, the first and second upward-facing intake orifices 45, 50 are positioned generally opposite each other about the edge of the mirror surface 40 such that each orifice 45, 50 is generally centered about a line CC that is perpendicular to the axis AA', which is parallel to the mirror surface 40 and coplanar to the longitudinal axis AA of the handle 15. As illustrated in FIG. 3, the upward-facing intake orifices 45, 50 are located in the housing 35 adjacent to the edge of the mirror 40. The upward-facing intake orifices 45, 50 are oriented to open generally in the same direction that the mirror surface 40 is facing. Thus, for the purposes of this specification, "upward-facing" is defined as facing in generally the same direction that the mirror surface 40 is facing.

As shown in FIG. 3, in one embodiment, the upward-facing intake orifices 45, 50 are positioned adjacent to the edge of the mirror surface 40. The center point or centroid C' for the first upward-facing intake orifice 45 is radially offset by angle $\beta$ about the edge of the mirror surface 40 in a first direction from the axis AA', and the center point or centroid C" for the second upward-facing intake orifice 50 is radially offset by angle $\gamma$ about the edge of the mirror surface 40 in a second direction from the axis AA'. As indicated in FIG. 4, the upward-facing intake orifices 45, 50 radially extend by angle δ about the edge of the mirror surface 40 from each side of the centroids C', C".

For example, in one embodiment, as indicated in FIG. 3, angles β and γ are each between approximately 45° and approximately 135°. In one embodiment, angles β and γ are each between approximately 50° and approximately 130°. In one embodiment, angles β and γ are each between approximately 55° and approximately 125°. In one embodiment, angles β and γ are each between approximately 60° and approximately 120°. In one embodiment, angles β and γ are each between approximately 65° and approximately 115°. In one embodiment, angles β and γ are each between approximately 70° and approximately 110°. In one embodiment, angles β and γ are each between approximately 75° and approximately 105°. In one embodiment, angles β and γ are each between approximately 80° and approximately 100°. In one embodiment, angles β and γ are each between approximately 85° and approximately 95°. Finally, in one angles β and γ are each approximately 90°.

In one embodiment, as indicated in FIG. 4, angle δ is between approximately 1° and approximately 90°. In one embodiment, angle δ is between approximately 5° and approximately 80°. In one embodiment, angle δ is between approximately 5° and approximately 70°. In one embodiment, angle δ is between approximately 5° and approximately 60°. In one embodiment, angle δ is between approximately 5° and approximately 50°. In one embodiment, angle δ is between approximately 5° and approximately 40°. In one embodiment, angle δ is between approximately 5° and approximately 35°. In one embodiment, angle δ is between approximately 5° and approximately 30°. In one embodiment, angle δ is between approximately 5° and approximately 25°. In one embodiment, angle δ is between approximately 5° and approximately 20°. In one embodiment, angle δ is between approximately 5° and approximately 15°. Finally, in one embodiment, angle δ is between approximately 10° and approximately 15°.

As shown in FIGS. 3 and 4, in one embodiment, the mirror surface 40 has a diameter E of between approximately 0.50 inches and approximately 1.50 inches, and the diameter F of the top edge 60 exceeds the diameter E of the mirror surface 40 by between approximately 0.02 inches and approximately 0.20 inches. For example, as illustrated in FIGS. 3 and 4, the mirror surface 40 has a diameter E of approximately 0.92 inches and the top edge 60 has a diameter F of approximately 1.00 inches. In one embodiment, the mirror surface 40 has a diameter E of between approximately 0.75 inches and approximately 1.25 inches. In one embodiment, the mirror surface 40 has a diameter E of between approximately 0.85 inches and approximately 1.15 inches.

In one embodiment, as illustrated in FIGS. 3 and 4, the housing 35 extends away from the top edge 60 to accommodate the upward-facing intake orifices 45, 50. As shown in FIG. 4, in one embodiment, the perimeters of the upward-facing intake orifices 45, 50 are comprised of an inward radius 70, an outward radius 75, and two end diameters 80. In one embodiment, the inward radius 70 is between approximately 0.25 inches and approximately 0.75 inches, the outward radius 75 is between approximately 0.12 inches and approximately 0.50 inches, and the end diameters 80 are between approximately 0.03 inches and approximately 0.12 inches. In one embodiment, as shown in FIGS. 3 and 4, the inward radius 70 is approximately 0.50 inches, the outward radius 75 is approximately 0.25 inches, the end diameters 80 are approximately 0.06 inches, and the center points used to define the end diameters 80 are separated by distance G, which is 0.30 inches.

To describe the configuration of another embodiment of the suction head 10, reference is now made to FIG. 5. FIG. 5 is a top view of another embodiment of the dental evacuation mirror 5, wherein the viewing direction is perpendicular to the mirror surface 40. As shown in FIG. 5, the housing 35 does not extend from the top edge 60 to accommodate the upward-facing intake orifices 45, 50, and the mirror surface 40 does not fully extend laterally (i.e., in a direction that is perpendicular to axis AA') to the top edge 60 of the housing 35. As illustrated in FIG. 5, the upward-facing intake orifices 45, 50 are located within the boundaries of the top edge 60. The perimeters of the upward-facing intake orifices 45, 50 are formed by the straight edge 85 of the mirror surface 40 intersecting the curved interior edge 90 of the top edge 60.

Figure 6:
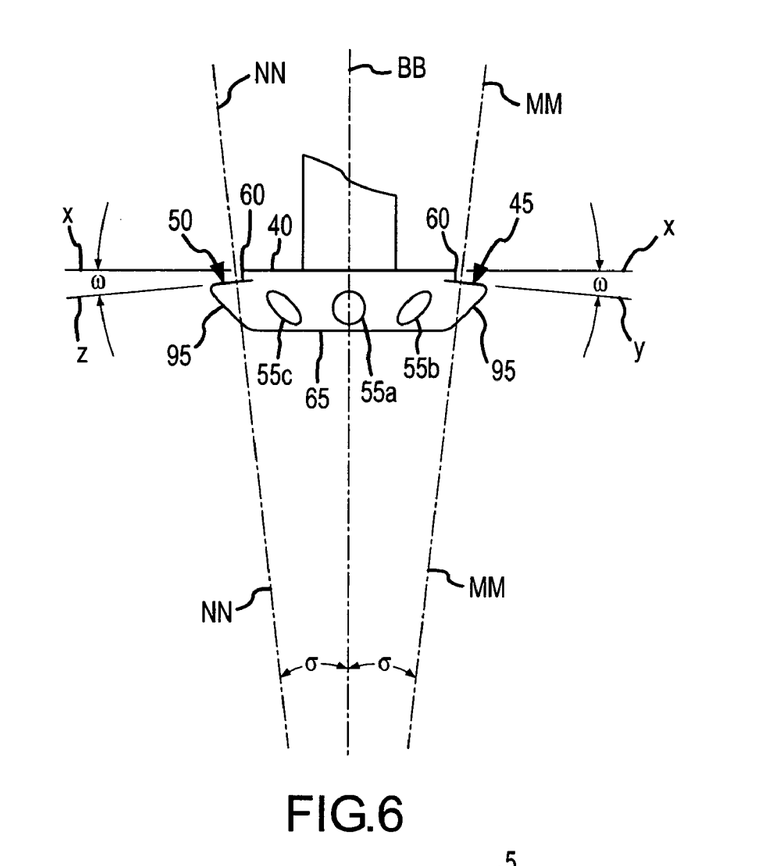
FIG. 6 is an end elevation of the dental evacuation mirror as viewed from the direction of arrow B in FIG. 3.

To further describe the forward-facing intake orifices 55 and the orientation of the upward-facing intake orifices 45, 50, reference in now made to FIGS. 2, 3 and 6. FIG. 6 is an end elevation of the dental evacuation mirror 5 as viewed from the direction of arrow B in FIG. 3.

As shown in FIG. 6, in one embodiment, the housing 35 of the suction head 10 has three forward-facing intake orifices 55. In other embodiments, the housing 35 will have a greater or lesser number of forward-facing intake orifices 55. In one embodiment, the forward-facing intake orifices 55 have a diameter of between approximately 0.05 inches and approximately 0.25 inches. In one embodiment, the forward-facing intake orifices 55 have a diameter of approximately 0.15 inches. For the purpose of this specification, "forward-facing" is defined as facing in a direction that is generally opposite the exit fluid pathway 17 and generally perpendicular to the direction faced by the mirror surface 40.

As illustrated in FIGS. 3 and 6, the center forward-facing intake orifice 55a is positioned on axis AA', the right forward-facing intake orifice 55b is positioned on axis DD, and the left forward-facing intake orifice 55c is positioned on axis EE. Axis AA' forms angle ε with axis DD and angle θ with axis EE. In one embodiment, angles ε and θ are each between approximately 15° and approximately 60°. In one embodiment, angles ε and θ are each between approximately 25° and approximately 55°. In one embodiment, angles ε and θ are each between approximately 35° and approximately 50°. In one embodiment, angles ε and θ are each between approximately 40° and approximately 50°. In one embodiment, angles ε and θ are each approximately 45°.

As illustrated in FIGS. 2 and 6, the housing 35 has sidewalls 95 that extend from the backside 65 to the top edge 60 or from the backside 65 to the edges of the upward-facing orifices 45, 50. As shown in FIGS. 2 and 6, the sidewalls 95 are beveled in that they slope from the backside 65 up and out to the top edge 60 or the edges of the upward-facing orifices 45, 50. In other words, in one embodiment, the angle formed by the backside 65 and the sidewalls 95 is obtuse. In other embodiments, the sidewalls 95 run essentially perpendicular to the mirror surface 40 from the backside 65 up to the top edge 60 or the edges of the upward-facing orifices 45, 50.

As shown in FIG. 6, the upward-facing intake orifices 45, 50 are oriented to face/open generally upward in the same direction faced by the mirror surface 40, which faces upward in the direction of axis BB. As illustrated in FIG. 6, the first upward-facing intake orifice 45 faces/opens generally upward in the direction of axis MM, and the second upward-facing intake orifice 50 faces/opens generally upward in the direction of axis NN. Axis BB forms angle σ with axis MM and axis NN.

In one embodiment, where angle σ is essentially 0° (i.e., axis MM and axis NN are essentially parallel to axis BB), the first and second intake orifices 45, 50 will face/open in a direction that is approximately perpendicular or normal to the mirror surface 40. In one embodiment, where angle σ is between approximately 0° and approximately 45°, the first and second intake orifices 45, 50 will face/open in a direction that is between approximately 0° and approximately 45° from being perpendicular or normal to the mirror surface 40. In one embodiment, where angle α is between approximately 0° and approximately 35°, the first and second intake orifices 45, 50 will face/open in a direction that is between approximately 0° and approximately 35° from being perpendicular or normal to the mirror surface 40. In one embodiment, where angle σ is between approximately 0° and approximately 25°, the first and second intake orifices 45, 50 will face/open in a direction that is between approximately 0° and approximately 25° from being perpendicular or normal to the mirror surface 40. In one embodiment, where angle σ is between approximately 0° and approximately 15°, the first and second intake orifices 45, 50 will face/open in a direction that is between approximately 0° and approximately 15° from being perpendicular or normal to the mirror surface 40. In one embodiment, where angle σ is between approximately 0° and approximately 10°, the first and second intake orifices 45, 50 will face/open in a direction that is between approximately 0° and approximately 10° from being perpendicular or normal to the mirror surface 40. In one embodiment, where angle σ is approximately 6°, the first and second intake orifices 45, 50 will face/open in a direction that is approximately 6° from being perpendicular or normal to the mirror surface 40.

As illustrated in FIG. 6, the mirror surface rests in plane X, the opening of the upward-facing intake orifice 45 rests in plane Y, and the opening of the upward-facing intake orifice 50 rests in plane Z. Plane X forms an angle ω with planes Y and Z. Plane Y is perpendicular to axis MM and plane Z is perpendicular to axis NN. In one embodiment, as shown in FIG. 6, planes Y and Z are offset back from plane X. In other embodiments, the planes X, Y, and Z are essentially coplanar with each other (i.e., they are not offset from each other).

In one embodiment, where the openings of the upward-facing intake orifices 45, 50 are essentially parallel with the mirror surface 40, the angle ω will be approximately 0°. In other embodiments, where the upward-facing intake orifices 45, 50 are oriented to face generally upward in the same direction faced by the mirror surface 40, but the are not essentially parallel with the mirror surface 40, the angle ω will be between approximately 0° and approximately 45°. In another embodiment, the angle ω will be between approximately 0° and approximately 35°. In another embodiment, the angle ω will be between approximately 0° and approximately 25°. In another embodiment, the angle ω will be between approximately 0° and approximately 15°. In another embodiment, the angle ω will be between approximately 0° and approximately 10°. In another embodiment, the angle ω will be approximately 6°.

Figure 8A:
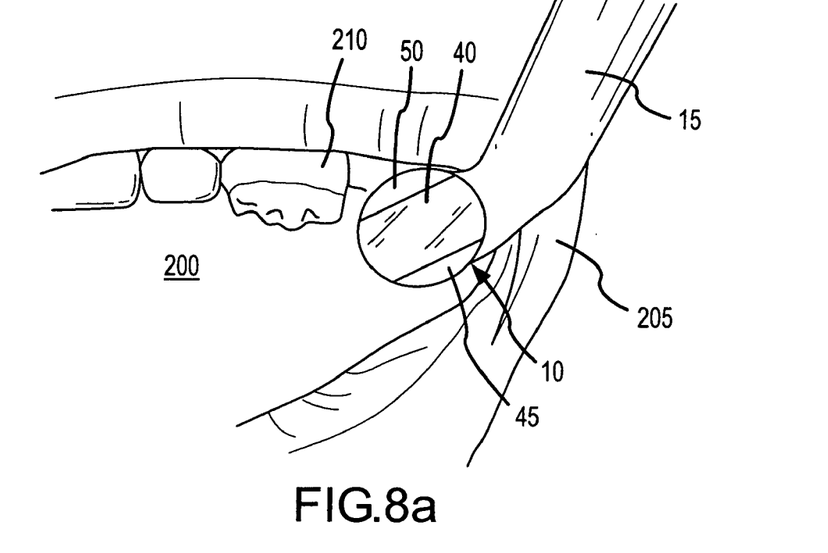
FIG. 8a is a photograph of the dental evacuation mirror being used to view the maxillary, posterior, left quadrant, buccal aspect of a patient's teeth.
Figure 8B:
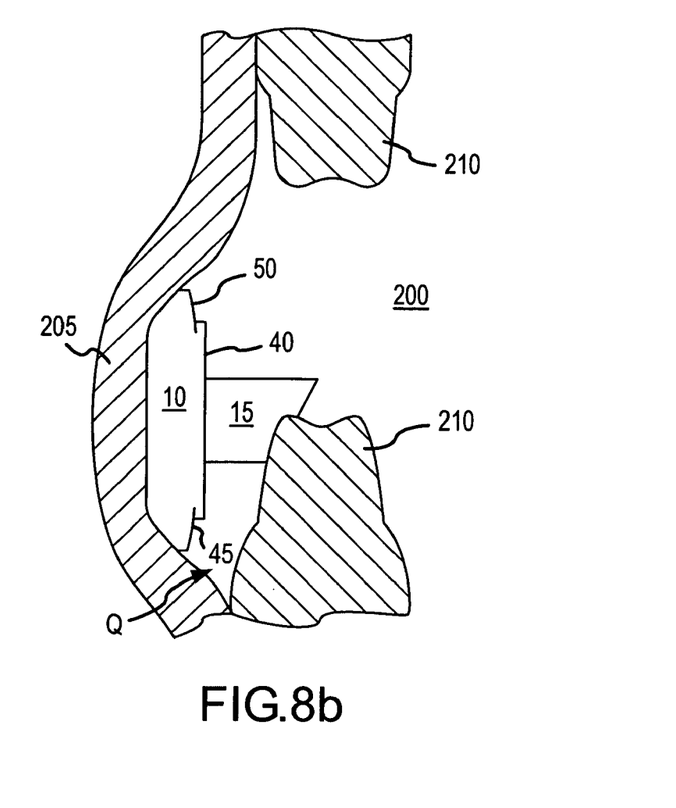
FIG. 8b is a sectional elevation taken through the side of a patient's mouth and showing the dental evacuation mirror retracting the cheek to place the dental evacuation mirror in position to view the mandibular, posterior, left quadrant, buccal aspect of the patient's teeth.
Figure 9A:
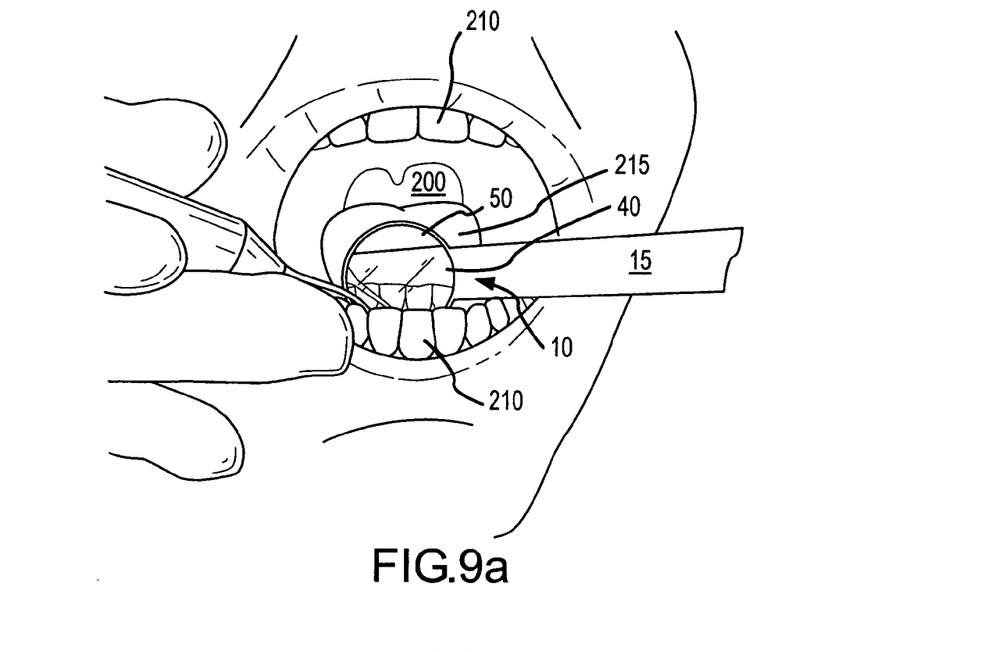
FIG. 9a is a photograph of the dental evacuation mirror being used to view the mandibular, anterior, lingual aspect of a patient's teeth.
Figure 9B:
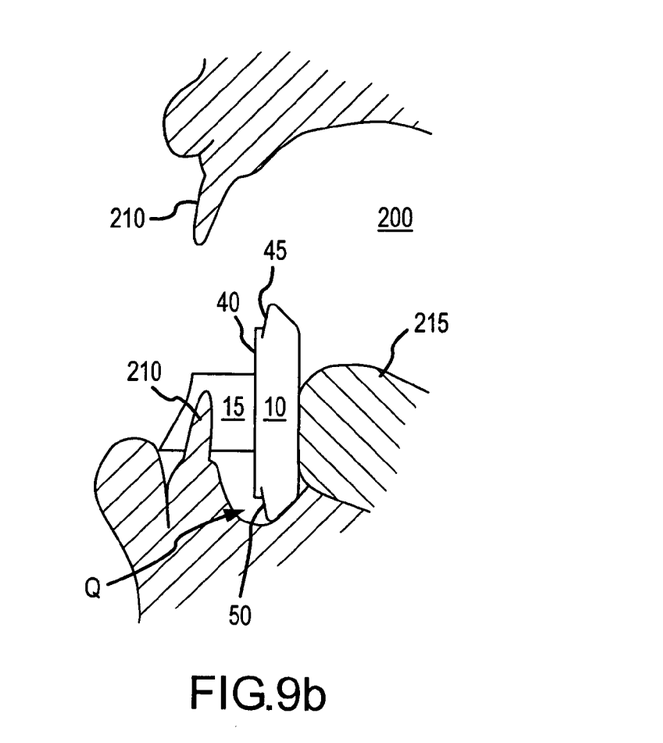
FIG. 9b is a sectional elevation taken through the front of a patient's mouth and showing the dental evacuation mirror retracting the tongue to place the dental evacuation mirror in position to view the mandibular, anterior, lingual aspect of the patient's teeth.

To illustrate some of the benefits of the present invention and to explain its operation, reference is now made to FIGS. 8a–9b. FIG. 8a is a photograph of the dental evacuation mirror 5 being used to view the maxillary, posterior, left quadrant, buccal aspect of a patient's teeth. FIG. 8b is a sectional elevation taken through the side of a patient's mouth 200 and showing the dental evacuation mirror 5 retracting the cheek 205 to place the dental evacuation mirror 5 in position to view the mandibular, posterior, left quadrant, buccal aspect of the patient's teeth 210. FIG. 9a is a photograph of the dental evacuation mirror 5 being used to view the mandibular, anterior, lingual aspect of a patient's teeth. FIG. 9b is a sectional elevation taken through the front of a patient's mouth 200 and showing the dental evacuation mirror 5 retracting the tongue 215 to place the dental evacuation mirror 5 in position to view the mandibular, anterior, lingual aspect of the patient's teeth 210.

When the dental evacuation mirror 5 is utilized, the end 25 of the handle 15 may be placed in fluid communication with a dental vacuum. A dental professional then holds the handle 15 of the dental evacuation mirror 5 and guides the suction head 10 into position inside the patient's mouth 200, as indicated in FIGS. 8a and 9a.

As shown in FIGS. 8a–9b, the suction head 10 may be positioned/oriented so the mirror surface 40 is facing the item (e.g., a tooth 210) being indirectly viewed via the mirror surface 40. If there is soft tissue (e.g., a cheek 205 or tongue 215) immediately adjacent to the item being viewed, the backside 65 of the housing 35 may be used to retract the soft tissue to provide adequate clearance between the mirror surface 40 and the item being viewed. Simultaneously, the intake orifices 45, 50, 55 may be used to evacuate liquids and debris that accumulate in the mouth during a dental procedure.

As shown in FIG. 8b, because of the configuration of the suction head 10 and the orientation of the upward-facing orifices 45, 50, the dental evacuation mirror 5 is able to retract the cheek 205 to view the buccal aspect of the teeth 210 without suctioning the soft tissue of the cheek 205 with the upward-facing orifices 45, 50. Thus, the upward-facing orifices 45, 50 are not obstructed by the cheek 205, which makes the dental evacuation mirror 5 more comfortable for the patient and more efficient at removing liquids and debris.

As shown in FIG. 9b, because of the configuration of the suction head 10 and the orientation of the upward-facing orifices 45, 50, the dental evacuation mirror 5 is able to retract the tongue 215 to view the lingual aspect of the teeth 210 without suctioning the soft tissue of the tongue 215 (or the soft tissue under the tongue 215) with the upward-facing orifices 45, 50. Thus, the upward-facing orifices 45, 50 are not obstructed by the tongue 215, which makes the dental evacuation mirror 5 more comfortable for the patient and more efficient at removing liquids and debris.

During dental procedures, fluids and debris tend to accumulate in the low spots and crevices of the mouth that are adjacent to the area of the mouth undergoing the procedure (e.g., areas Q in FIGS. 8b and 9b). As indicated in FIGS. 8b and 9b, because of the configuration of the dental evacuation mirror 5, the upward-facing intake orifices 45, 50 are ideally positioned/oriented to evacuate the low spots and crevices (areas Q) without suctioning the surrounding soft tissues 205, 215 or requiring the dental professional to contort his arm excessively to access the fluids and debris in those areas Q.

Although the present invention has been described with reference to preferred embodiments, persons skilled in the art will recognize that changes may be made in form and detail without departing from the spirit and scope of the invention.

We claim:

1. A dental evacuation tool for being placed in fluid communication with a dental vacuum, the tool comprising:

a suction head including a mirror surface, first and second upward-facing intake orifices adjacent the mirror surface, and an exit fluid pathway that is in fluid communication with the first and second upward-facing intake orifices; and an elongated tubular handle including a first end adapted to be in fluid communication with the vacuum and a second end in fluid communication with the exit fluid pathway, wherein the first and second upward-facing intake orifices are positioned generally opposite each other about the mirror surface and are generally centered about a line that is generally perpendicular to the longitudinal axis of the handle, wherein the first and second upward-facing intake orifices open in generally the same direction faced by the mirror.

2. The tool of claim 1 wherein the suction head further includes a forward-facing intake orifice in fluid communication with the exit fluid pathway and positioned on the suction head generally opposite the exit fluid pathway.

3. The tool of claim 2 wherein the forward-facing intake orifice opens in a direction that is generally perpendicular to the mirror surface.

4. The tool of claim 1 wherein the suction head further includes a sidewall, a backside that is generally opposite the mirror surface, and at least two forward-facing intake orifices located in the sidewall generally opposite the exit fluid pathway.

5. The tool of claim 4 wherein the backside and the sidewall form an obtuse angle.

6. A method of making a dental evacuation tool for being placed in fluid communication with a dental vacuum, the method comprising:

providing a suction head including a mirror surface and an exit fluid pathway;

providing an elongated tubular handle including a first end in fluid communication with the exit fluid pathway and a second end adapted to be in fluid communication with the vacuum and;

providing first and second upward-facing intake orifices on the suction head adjacent to the mirror surface such that the upward-facing intake orifices are in fluid communication with the exit fluid pathway, and the first and second upward-facing intake orifices are positioned generally opposite each other about the mirror surface and are generally centered about a line that is generally perpendicular to the longitudinal axis of the handle, wherein the first and second upward-facing intake orifices open in generally the same direction faced by the mirror.

7. The method of claim 6 further comprising providing a forward-facing intake orifice on the suction head such that the forward-facing intake orifice is in fluid communication with the exit fluid pathway and positioned on the suction head generally opposite the exit fluid pathway.

8. The method of claim 7 wherein the forward-facing intake orifice opens in a direction that is generally perpendicular to the mirror surface.

9. The method of claim 6 further comprising providing on the suction head a sidewall, a backside that is generally opposite the mirror surface, and at least two forward-facing intake orifices located in the sidewall generally opposite the exit fluid pathway.

10. The method of claim 9 wherein the backside and the sidewall form an obtuse angle.

* * * * *